United States Patent [19]

Jovánovics et al.

[11] 4,172,077

[45] Oct. 23, 1979

[54] PROCESS FOR THE ISOLATION OF ALKALOID COMPONENTS FROM THE PLANT VINCA ROSEA L.

[75] Inventors: Karola Jovánovics; György Fekete; Eszter Dezséri; Lajos Dancsi; Csaba Lörincz; Béla Szarvady; György Dobo; Csaba Szántay; Lajos Szabó, all of Budapest, Hungary

[73] Assignee: Richter Gedeon Vegyeszeti Gyar RT, Budapest, Hungary

[21] Appl. No.: 908,584

[22] Filed: May 22, 1978

[30] Foreign Application Priority Data

May 31, 1977 [HU] Hungary .................. RI 638

[51] Int. Cl.$^2$ .................. C07D 519/04; C07D 215/00; C07G 5/00
[52] U.S. Cl. .................. 260/244.4; 546/51
[58] Field of Search .................. 260/236 R, 244.4; 424/195; 546/51

[56] References Cited

U.S. PATENT DOCUMENTS

| 3,097,137 | 7/1963 | Beer et al. | 260/236 R |
|---|---|---|---|
| 3,205,220 | 9/1965 | Svoboda et al. | 260/236 R |
| 3,225,030 | 12/1965 | Svoboda | 260/236 R |
| 3,352,868 | 11/1967 | Neuss et al. | 260/236 R |
| 3,370,057 | 2/1968 | Svoboda et al. | 260/236 R |
| 3,392,173 | 7/1968 | Hargrove | 260/236 R |
| 3,422,112 | 1/1969 | Gorman et al. | 260/236 R |

OTHER PUBLICATIONS

Svoboda et al., J. of Pharm. Sci., Aug. 1962, vol. 51, No. 8, pp. 707-720.

*Primary Examiner*—Donald B. Moyer
*Attorney, Agent, or Firm*—Karl F. Ross

[57] ABSTRACT

Tumor inhibiting alkaloids are recovered from Vinca Rosea L. by a method which comprises extracting the dried leaves with a solvent selected from the group consisting of an alkanol having 1 to 5 carbon atoms, a mixture of an alkanol having 1 to 5 carbon atoms and a dilute, aqueous solution, benzene and benzene homologs; subsequently purifying the alkaloid extract obtained by a phase-change method between immiscible solvents, precipitating the main amount of dimeric alkaloids in form of their sulphuric acid addition salts, isolating leurosine, vincistine, vinblastine, desacetoxy-vinblastine, N-desmethyl-vinblastine and desacetyl-vinblastine from the salt mixture obtained, and then completing the separation and isolation of the remaining alkaloids by separation and isolation by adjusting the pH-value of the mother liquor, after precipitation and removal of the salt mixture, to 5.5 to 10, extracting the solution with a water-immiscible organic solvent and separating vindoline, catharantine, 3',4'-anhydrovinblastine and leurosine from the extract by chromatography, extracting vindoline in the pH-range of 2.5 to 3.5 and catharantine 3',4'-anhydrovinblastine and leurosine in the pH-range of 5 to 6 with benzene or a benzene homologue, from the mother liquor obtained when isolating the salt mixture, and separating a mixture of leurosine and 3',4'-anhydrovinblastine by crystallization, epoxidizing this mixture with an oxygen source, or separating the mixture into its components by chromatography, and subsequently epoxidizing the 3',4'-anhydrovinblastine component to leurosine, and isolating catharantine remaining from the mother liquor obtained when separating the crystalline mixture, or separating the extract containing catharantine, 3',4'-anhydrovinblastine and leurosine into its components by chromatography.

5 Claims, No Drawings

PROCESS FOR THE ISOLATION OF ALKALOID COMPONENTS FROM THE PLANT VINCA ROSEA L.

This invention relates to a new process for the isolation of alkaloid components from the plant *Vinca rosea* L. More particularly, this invention relates to a process for the large-scale isolation of native catharantine, vindoline and 3',4'-anhydrovinblastine whereby the isolation of vincristine, vinblastine, leurosine and the corresponding desacetoxy, desacetyl and N-desmethyl derivatives in a manner known per se can also be accomplished.

For the isolation of the two monoindole alkaloids: vindoline and catharantine from the dried plant *Vinca rosea* L. Svoboda [J. Am. Pharm. Assoc. 48, (11), 659 (1959)] described a method, which can be accomplished only with a very modest yield. From 1 kg. of the dried plant—subjecting the whole plant to a suitable treatment—approximately 0.6 g. of vindoline and 0.05 g. of catharantine were obtained.

3',4'-anhydrovinblastine until now has neither been isolated from the plant *Vinca rosea* L. nor identified in it.

For the preparation of the diindole alkaloid components starting from the leaves of *Vinca rosea* L. there are more methods known in the art (U.S. Pat. nos. 3,097,137; 3,205,220; 3,225,030 and Hungarian Pat. Nos. 153,200; 154,715; 160,967 and 164,958 as well as Austrian Pat. Nos. 313,435, 313,485, Australian pat. No. 458,629 and Swiss Pat. No. 572,488 and British Pat Nos. 1,412,932, 1,382,460 corresponding to the preceding two patents). According to these known processes from 1 kg. of the dried leaves of *Vinca rosea* L. about 0.1 to 0.2 g. of leurosine can be obtained and vinblastine, vincristine and optionally the corresponding N-desmethyl, desacetyl and desacetoxy derivatives are also simultaneously isolated.

Further on it is well known that the synthetic catharantine and vindoline may be coupled by the Polonovszky reaction to give 3',4'-anhydrovinblastine which can thereafter be epoxidized to leurosine [Potier et al. Tetrahedron Letters 3945 (1976); DT-OS 25 58,124; Helv. Chim. Acta 59, 2858 (1976); Heterocycles 4, 997 (1976), Belgian patent specification No. 842,200 equivalent to U.S. patent application Ser. No. 582,372]. Leurosine itself has a valuable tumour growth inhibiting activity and the N-desmethyl-N-formyl derivative thereof is the most promising substance against leukemia (Hungarian Pat. No. 165,986 equivalent to U.S. patent application Ser. No. 422,100, and Austrian Pat. No. 332,566 which has issued as British Pat. No. 1,412,932).

The object of the present invention is to provide a suitable method for an industrial-scale isolation of alkaloid derivatives from the plant *Vinca rosea L.*, which can be utilized as native starting materials for the synthesis of N-desmethyl-N-formyl-leurosine, so that also the other dimeric alkaloids can be isolated in an unchanged quantity and quality.

It has now been found that extracting the dried leaves with an alkanol having 1 to 5 carbon atoms or with a mixture of same and a dilute aqueous acid solution and/or benzene or its homologues, and subsequently purifying the extract obtained containing the mixture of the alkaloids by a phase-change method, the main amount of the dimeric alkaloids (vincristine, vinblastine, leurosine and the corresponding desacetoxy, desacetyl and N-desmethyl derivatives) can be precipitated in the form of their sulphate salts in a manner known per se and the components of the salt mixture can be separated from each other. From the mother liquor obtained when separating the salt mixture vindoline, catharantine and a considerable amount of leurosine as well as 3',4'-anhydrovinblastine—which has not been separated before from the plant—can be isolated. The 3',4'-anhydrovinblastine so obtained can be epoxidized into leurosine in a conventional manner. Following this procedure from 1 kg. of dried leaves altogether approximately 0.4 to 0.5 g. of leurosine, 0.4 g. of catharantine and 0.8 g. of vindoline can be prepared. This yield is many times of the yield achieved by the known processes, which is a considerable advantage in view of the therapeutic importance and high prices of these materials.

The invention relates to a process for the isolation of native vindoline, catharantine, 3',4'-anhydrovinblastine and vincristine, vinblastine, leurosine and the corresponding desacetoxy, desacetyl and N-desmethyl derivatives from the plant *Vinca rosea L.*, by extracting the dried leaves with a $C_{1-5}$ alkanol or optionally with a mixture of a $C_{1-5}$ alkanol and a dilute, aqueous acid solution and/or benzene or benzene homologue, and purifying the alkaloid extract by phase-change methods in a manner known per se, precipitating the main amount of dimeric alkaloids in form of their sulphuric acid addition salts and separating the leurosine, vincristine, and vinblastine, and, if desired, desacetoxy-vinblastine, N-desmethyl-vinblastine and desacetyl-vinblastine in a manner known per se, and thereafter.

(a) adjusting the pH-value of the mother liquor, obtained after isolating the salt mixture, to 5.5 to 10, extracting this solution with a water-immiscible organic solvent and separating the vindoline, catharantine, 3',4'-ahydrovinblastine and leurosine from the extract by chromatography; or (b) extracting vindoline in the pH-range of 2.5 to 3.5 and catharantine 3',4'-anhdryo-vinblastine and leurosine in the pH-range of 5 to 6 with benzene or a benzene homologue and from the latter extract (b₁) separating a mixture of 3',4'-anhydrovinblastine and leurosine by crystallization, epoxidizing the mixture in a manner known per se or separating the same into the components thereof by chromatography, then epoxidizing the 3',4'-anhydrovinblastine and finally isolating catharantine from the mother liquor obtained when separating the crystalline mixture; or (b₂) separating the extract containing 3',4'-anhydrovinblastine, catharantine and leurosine into its components by chromatography.

According to the process provided by the invention dried-leaves are extracted with an alkanol having 1 to 5 carbon atoms, such as methanol, ethanol, iso- and n-propanol, butanol etc. Preferably methanol is employed or the extraction is carried out with a mixture of methanol or another alkanol having 1 to 5 carbon atoms with a dilute aqueous acid solution, preferably a 2 to 3% aqueous solution of sulphuric acid or tartaric acid and benzene or a benzene homologue, preferably toluene. When the extraction is performed with a two-phase solvent system containing, in addition to an aqueous-alcoholic phase, also benzene or benzene homologues. This latter organic phase is separated after extraction, shaken with a dilute aqueous acid solution (in order to transfer all the alkaloids into the aqueous acid phase) and the aqueous acid phase is combined with the original aqueous acid phase. On the other hand, when extraction is carried out without benzene it is advisable to clear the aqueous acid phase from chlorophyll and other organic odouring agents by extraction with an organic acid solvent, preferably with benzene. The pH of the chlorophyll-free alkaloid solution is thereafter adjusted to 5.5 to 10, preferably 8.5 to 9 and the alkaloids are extracted with an organic solvent, for instance benzene or a benzene homologue or a chlorinated hydrocarbon. From the organic phase is separated the overwhelming mass of the diindole alkaloids precipitated according to the process disclosed in the Hungarian Pat. No. 160,967 or Australian Pat. No. 458,629, preferably in form of a sulphuric acid addition salt.

From the salt mixture obtained, the individual diindole alkaloids are then separated in a manner known per se, Vincristine and vinblastine can for instance be separated as described in the said Hungarian Pat. No. 160,967 or its Australian equivalent.

According to another method, the mixture of the acid addition salts, preferably sulphate salts of diindole alkaloids is dissolved in an organic solvent, expediently in acetone or in an alyphatic alcohol having 1 to 5 carbon atoms, preferably methanol, at 0° to 50° C., preferably at room temperature.

Diindole alkaloid bases are precipitated from the solution by means of a base, such as monoethylamine, diethylamine or pyridine. The leurosine base is precipitated from the solution at 0° to 25° C.

The mother liquor obtained after separating the precipitated leurosine base is evaporated under reduced pressure. The evaporation residue is dissolved in an organic solvent, preferably in benzene or a benzene homologue, such as toluene or xylene, more preferably benzene. Simultaneously with the dissolution of the residue, the sulphate of the organic base used for the liberation of the diindole alkaloids (monomethylamine, diethylamine, pyridine) is precipitated from the solution and filtered off. The filtrate is then extracted with a phosphate-buffer having a pH-value of 3.7 to 4.3, preferably 4±0.1. The acid aqueous extracts are combined and their pH-value is adjusted to 3.5 to 4.1, preferably 4.0±0.1 with an acid, preferably phosphoric acid. The acid aqueous solution obtained is extracted with an chlorinated hydrocarbon, preferably methylene chloride, and vinblastine is then separated by evaporating the methylene chloride extract.

The pH of the aqueous phase is adjusted to 7.5 to 10, preferably to 8.5 to 9 and vincristine, N-desmethyl-vinblastine and 4-desacetoxy-vinblastine are extracted with a water-immiscible organic solvent, preferably a chlorinated hydrocarbon. By formylating the alkaloid mixture, N-desmethyl-vinblastine is transformed into vincristine. The pH-value of the alkaloid mixture consisting now of three components is adjusted again to 7.5 to 10 and the alkaloids are extracted with an organic solvent or solvent mixture, preferably with a mixture of a benzene homologue—including benzene—and a chlorinated hydrocarbon, preferably in a mixture of benzene and chloroform and the solution obtained is subjected to column chromatography. As adsorbent, alumina, preferably partly deactivated alumina is used, and elution therefrom is carried out expediently with an organic solvent mixture, preferably various mixtures of benzene and chloroform. The alkaloids contained in the fractions obtained after column chromatography are preferably identified by thin layer chromatography. The eluates containing the same alkaloid component are combined. The fractions in which vincristine and vinblastine are present then are subjected to a treatment known per se to separate these alkaloids, while the fractions in which 4-desacetoxy-vinblastine is detected are combined and subsequently evaporated in vacuo. If desired, this crude 4-desacetoxy-vinblastine residue can be purified by crystallization.

From the mother liquor obtained when the diindole alkaloids are filtered off, a further considerable amount of leurosine, catharantine, vindoline as well as 3',4'-anhydrovinblastine can be obtained following either reaction variant (a) or (b) according to the invention.

According to process variant (a) the pH value of the mother liquor is adjusted to 6 to 10 and the above-listed four alkaloids are extracted with an organic solvent, expediently with benzene or a homologue thereof, or a chlorinated hydrocarbon or an aliphatic ether. The alkaloid mixture obtained is separated to its components by column chromatography carried out on a partly desactivated alumina column. Elution is performed with benzene and subsequently with a mixture of benzene and a chlorinated hydrocarbon.

When following the process variant (b) according to the invention the mother liquor is at first acidified to a pH value of 2.5 to 3.5 and the vindoline is extracted from the acid mixture obtained with benzene of a homologue thereof. The organic extract is then separated, evaporated and optionally purified for example by decolouring and/or recrystallization to give vindoline. The pH of the acid aqueous phase is thereater adjusted to 5 to 6 and the three alkaloids remaining therein are extracted with benzene or a homologue thereof. The extract is either subjected to chromatography (process variant $b_2$/) on a column made of partly desactivated alumina for elution using benzene or a homologue thereof, and subsequently a mixture of benzene and a chlorinated hydrocarbon or is processed according to the process variant ($b_1$).

When proceeding according to the process variant ($b_1$) the extract containing the three alkaloid components is evaporated. The evaporation residue is crystallized from an organic solvent, preferably an alcohol having 1 to 5 carbon atoms. A crystal mixture of leurosine and 3',4'-anhydrovinblastine is obtained and the catharantine remains dissolved in the mother liquor.

The crystal mixture obtained is preferably epoxidized in situ, without previous separation of the leurosine. By epoxidation, the 3', 4'-anhydrovinblastine is transformed into leurosine, i.e., the total alkaloid content of the crystal mixture will be present in form of leurosine, Epoxidation is preferably carried out with organic hydroperoxides, for instance with coumyl-hydroperoxide or tert.-butyl-hydroperoxide, or with alkali metal hypohalogenites or oxygen, expendiently originating from the air. When epoxidation is performed with oxygen, the reaction proceeds practically in any organic solvent. Representatives of suitable organic solvents are tetrahydrofuran (THF) or an organic amino compound, preferably dimethyl formamide (DMF). When organic peroxides are sued for epoxidation, the reaction is preferably performed in a nitrile-type solvent. If desired, promotors, such as metal complexes, metal or metal oxide catalysts or radical initiators containing a nitrile and/or azo group can also be present in the reaction mixture.

The crystal mixture can be separated into its components by chromatography, whereby the leurosine is isolated and, if desired, the 3′,4′-anhydrovinblastine is epoxidized into leurosine as described above.

When the components are separated from each other by means of column chromatography, the eluate fractions obtained are analysed by thin layer chromatography using silica gel as an adsorbent and a 5:0.5 mixture of methylene chloride and methanol as a solvent mixture. Thin layer chromatography can be carried out also as described in the U.S. Pharmacopeia XVIII.

Further details of the invention are illustrated by the following non-limiting Examples.

EXAMPLE 1

(A) One kg. of ground dried leaves of *Vinca rosea L.* is made wet with a mixture of one lit. of methanol and 0.25 lit. of a 2% aqueous sulphuric acid solution. 5 lit. of toluene are added and the mixture is stirred for 1.5 hours. The toluene extraction is repeated three more times with the same amounts of toluene. The toluene phases are then separated, combined and extracted with three 5-lit. portions of a 2% aqueous sulphuric acid solution until no alkaloid traces can be detected. The acid aqueous solutions are combined and chlorophyll and other colouring agents are extracted with two 1-lit. portions of benzene. The aqueous phase is separated and its pH-value adjusted to 8.5 to 9 with aqueous ammonium hydroxide solution. The alkaline solution is then extracted with four 1-lit. portion of benzene, the benzene extract are combined, dried with sodium sulphate, filtered and the filtrate evaporated to dryness. An alkaloid base mixture is obtained weighing approximately 10 g. which is then treated with sulphuric acid in ethanol in a manner known per se to give a mixture of the sulphates of the diindole alkaloids (vincristine, leurosine, vinblastine, desacetoxy-vinblastine, N-desmethyl-vinblastine and desacetyl-vinblastine). The weight of the sulphate salt mixture amounts to 0.73 g. from which 0.18 g. of leurosine—m.p. 202 to 204° C.; $(\alpha)_D^{20} = +79.4°$; c=1, chloroform)—and a usual amount of the above diindole alkaloids are obtained in a conventional manner.

(B) The mother liquor I obtained from the filtration of the above salt mixture (about 100 ml.) is diluted with 1.5 lit. of water and subsequently adjusted to pH 2.7 to 3.0. The acid solution obtained is extracted with five 1-lit. portions of benzene and the phases are allowed to separate. The acid phases are combined and put aside (mother liquor II). The benzene extracts are combined, dried with sodium sulphate, filtered and the filtrate evaporated to dryness. The evaporation residue is dissolved in 12 ml. of benzene, shaken with 0.5 g. of activated coal and passed through an alumina layer (activity grade III). The layer is then washed with 150 to 200 ml. of benzene. The benzene filtrate is evaporated, the evaporation residue dissolved in 5 ml. of ether and the precipitated crystals are filtered, washed with two 1 ml. portions of ether and finally dried.

Yield: 0.8 g. of vindoline melting at 167° to 168° C.; $(\alpha)_D^{20} = -28.5°$ (c=1, chloroform).

(C) The pH-value of the mother liquor II is adjusted to 5.5 with dilute aqueous ammonium hydroxide solution and the solution is extracted with three to five 1-lit. portions of benzene. The progress of the extraction is monitored by thin layer chromatography and the solution to be extracted is adjusted to pH 5.5 before the addition of each benzene portion. The benzene extracts are combined, evaporated and the evaporation residue crystallized from methanol. The crystals are filtered off and the methanolic mother liquor is put aside until further treatment. Yield: 0.35 g. of a 1:1 mixture of leurosine and 3′,4′-anhydrovinblastine.

(D) The product mixture obtained in the Example 1 c) is epoxidized with oxygen from the air in a dimethyl formamide medium, in a manner known per se and the leurosine obtained is separated from the reaction mixture. Yield: 0.25 g. of leurosine having the same quality as 0.18 g. of leurosine obtained in Example 1 A).

(E). The methanolic mother liquor obtained after crystallization of leurosine and anhydrovinblastine (Example 1 C/) is evaporated. The evaporation residue is dissolved in 12 ml. of benzene and the benzene solution is chromatographed on column prepared from 100 g. alumina having an activity grade III and treated with benzene. Catharantine is eluted with benzene collecting 50-ml. fractions of eluate. The progress of the eluation is monitored by thin layer chromatography. The catharantine is mainly contained in the 4th fraction.

Fractions containing catharantine are combined and subsequently evaporated to dryness. The residue is dissolved in a 1.25% solution of sulphuric acid in ethanol (pH 4.5 to 5.0) and allowed to crystallize overnight. The crystals are filtered off, washed with 1 to 2 ml. of ethanol and dried.

Yield: 0.41 g. of catharantine sulphate; $(\alpha)_D^{20} = +58°$ (c=1.96% ethanol).

EXAMPLE 2

Mother liquor I obtained when filtered the dimeric alkaloid sulphate salt mixture prepared from 1 kg. of dried leaves according to Example 1A) (about 100 ml.) is diluted with 1.5 lit. of water and its pH-value is adjusted to 8.5 to 9 with a concentrated aqueous ammonium hydroxide solution. The alkaline solution obtained is extracted with four 1-lit. portions of benzene, the combined benzene extracts are dried with sodium sulphate, filtered and the filtrate evaporated. The evaporation residue is dissolved in 55 ml. of benzene and the solution is chromatographed on a column prepared from 450 g. of alumina having an activity grade III with benzene. For elution 2 lit. of benzene and subsequently 4.5 lit. of a 3:2 mixture of benzene and chloroform are used. 200-ml. fractions are collected and tested for alkaloid content by thin layer chromatography. The first four fractions are free from alkaloids. The fractions 5 to 9 contain catharantine, the fractions 21 to 26 vindoline and the fractions 27 and 28 the mixture of vindoline and 3′,4′-anhydrovinblastine. In the 29th to 24th fractions leurosine is detected. The eluate fractions containing the same alkaloid are combined and evaporated to dryness. Yield: 0.57 g. of catharantine from which 0.52 g. of the corresponding sulphate can be prepared (5th to 9th fractions);

0.145 g. of 3′,4′-anhydro-vinblastine (from the 27th to 28th fractions, crystallized from methanol), m.p. 212° to 214° C.; $(\alpha)_D^{20} = +64.2°$ (c=0.5, chloroform).

0.125 g. of leurosine (from the 29th to 34th fractions, crystallized from methanol).

0.78 g. of vindoline (evaporating the methanolic mother liquor of 3′,4′-anhydrovinblastine and the 21st to 26th fractions and crystallizing the product obtained from ether).

EXAMPLE 3

0.145 g. of 3′,4′-anhydrovinblastine are dissolved in 20 ml of dimethyl formamide. A slow oxygen stream is bubbled through the solution for 10 minutes and the mixture is allowed to stand at room temperature for 16 to 20 hours. A concentrated ammonium hydroxide solution is then added to the reaction mixture to adjust the pH-value to 8.5 and the alkaline mixture is extracted with three 25-ml. portions of benzene. The combined benzene extracts are dried with sodium sulphate, filtered and the filtrates evaporated. The evaporation residue is crystallized from 1 ml. of methanol. Yield: 0.11 g. (75%) of leurosine.

What we claim is:

1. Process for the isolation of native vindoline, catharantine, 3',4'-anhydrovinblastine, vincristine, vinblastine, leurosine and the corresponding desacetoxy, desacetyl and N-desmethyl derivatives from the dried plant *Vinca rosea L.* which comprises the steps of extracting the dried leaves with a solvent selected from the group consisting of an alkanol having 1 to 5 carbon atoms, a mixture of an alkanol having 1 to 5 carbon atoms and a dilute, aqueous acid solution, benzene and benzene homologs, subsequently purifying the alkaloid extract obtained by a phase-change method between immiscible solvents, precipitating the main amount of dimeric alkaloids in form of their sulphuric acid addition salts, isolating leurosine, vincristine, vinblastine, desacetoxy-vinblastine, N-desmethyl-vinblastine and desacetylvinblastine from the salt mixture obtained, and then completing the separation and isolation of the remaining alkaloids by separation and isolation by adjusting the pH-value of the mother liquor, after precipitation and removal of the salt mixture, to 5.5 to 10, extracting the solution with a water-immiscible organic solvent and separating vindoline, catharantine, 3',4'-anhydrovinblastine and leurosine from the extract by chromatography.

2. The process defined in claim 1 wherein the extraction of the dried leaves of *Vinca rosea L.* is carried out with methanol at room temperature.

3. The process defined in claim 1 which comprises adjusting the pH-value of the mother liquor to pH=8.5 to 9.

4. Process for the isolation of native vindoline, catharantine, 3',4'-anhydrovinblastine, vincristine, vinblastine, leurosine and the corresponding desacetoxy, desacetyl and N-desmethyl derivatives from the dried plant *Vinca rosea L.* which comprises the steps of extracting the dried leaves with a solvent selected from the group consisting of an alkanol having 1 to 5 carbon atoms, a mixture of an alkanol having 1 to 5 carbon atoms and a dilute, aqueous acid solution, benzene and benzene homologs, subsequently purifying the alkaloid extract obtained by a phase-change method between immiscible solvents, precipitating the main amount of dimeric alkaloids in form of their sulphuric acid addition salts, isolating leurosine, vincristine, vinblastine, desacetoxy-vinblastine, N-desmethyl-vinblatine and desacetyl-vinblastine from the salt mixture obtained, and then completing the separation and isolation of the remaining alkaloids by separation and isolation by extracting vindoline in the pH-range of 2.5 to 3.5 and catharantine 3',4'-anhydrovinblastine and leurosine in the pH-range of 5 to 6 with benzene or a benzene homologue, from the mother liquor obtained when isolating the salt mixture, and separating a mixture of leurosine and 3',4'-anhydrovinblastine by crystallization, epoxidizing this mixture with an oxygen source, or separating the mixture into its components by chromatography, and subsequently epoxidizing the 3',4'-anhydrovinblastine component to leurosine, and isolating catharantine remaining from the mother liquor obtained when separating the crystalline mixture; or separating the extract containing catharantine, 3',4'-anhydrovinbaastine and leurosine into its components by chromatography.

5. The process defined in claim 4 wherein the extraction of the dried leaves of *Vinca rosea L.* is carried out with methanol at room temperature.

* * * * *